(12) United States Patent
Duhr et al.

(10) Patent No.: US 9,389,211 B2
(45) Date of Patent: Jul. 12, 2016

(54) DEVICE FOR DETECTING PROPERTIES OF CHEMICAL AND/OR BIOLOGICAL FLUIDS

(71) Applicants: NanoTemper Technologies GmbH, Munich (DE); Hirschmann Laborgerate GmbH & Co. KG, Eberstadt (DE)

(72) Inventors: Stefan Duhr, Munich (DE); Philipp Baaske, Munich (DE); Hans-Jurgen Bigus, Pliezhausen (DE)

(73) Assignees: Nanotemper Technologies GmbH, Munich (DE); Hirschmann Laborgerate GmbH & Co. KG, Eberstadt (DE)

( * ) Notice: Subject to any disclaimer, the term of this patent is extended or adjusted under 35 U.S.C. 154(b) by 0 days.

(21) Appl. No.: 13/624,473

(22) Filed: Sep. 21, 2012

(65) Prior Publication Data

US 2013/0089921 A1 Apr. 11, 2013

(30) Foreign Application Priority Data

Sep. 23, 2011 (EP) .................................... 11182639

(51) Int. Cl.
*G01N 21/75* (2006.01)
*G01N 33/00* (2006.01)
(Continued)

(52) U.S. Cl.
CPC ............... *G01N 33/00* (2013.01); *B01L 3/5082* (2013.01); *B01L 9/00* (2013.01); *B01L 2300/0832* (2013.01); *G01N 21/03* (2013.01); *G01N 2021/0346* (2013.01)

(58) Field of Classification Search
CPC .......... G01N 33/00; G01N 2021/0346; G01N 21/03; B01L 9/00; B01L 3/5082; B01L 2300/0832

USPC ............ 422/50, 400, 401, 402, 403, 404, 405, 422/408, 62, 63, 64, 65, 67, 68.1, 73, 75, 422/82.05, 82.06, 82.07, 82.08, 82.09, 98, 422/500, 501, 504, 509, 510, 511, 512, 514, 422/515, 521, 526, 547, 549, 550, 554, 556, 422/557, 558, 559, 560, 561, 562, 565, 566, 422/939, 940; 436/43, 46, 47, 164, 165, 436/169, 170, 815, 817; 435/13, 283.1, 435/287.1, 287.7, 287.8, 287.9, 288.7
See application file for complete search history.

(56) References Cited

U.S. PATENT DOCUMENTS 3,847,274 A * 11/1974 Inglish .................. B65D 83/02
206/443
3,932,131 A * 1/1976 Rolfo-Fontana ................ 436/45
(Continued)

OTHER PUBLICATIONS

Communication prusuant to Article 94(3) EPC for European Patent Application No. 11 182 639.2-1356, dated Oct. 24, 2013, 4 pages.
(Continued)

*Primary Examiner* — Dennis M White
(74) *Attorney, Agent, or Firm* — Westman, Champlin & Koehler, P.A.

(57) ABSTRACT

The present invention relates to a device for investigating, measuring and/or detecting properties of chemical and/or biological fluids as well as to a device for performing these procedures and a system comprising a holder for holding at least one of said devices. A device for detecting properties of chemical and/or biological fluids may comprise a tubular structure with a cavity for accommodating the fluid, the tubular structure comprising a magnetizable and/or magnetic material, wherein the tubular structure comprises a segment that is transparent to light of wavelength 200 nm to 2000 nm.

19 Claims, 5 Drawing Sheets (51) Int. Cl.
  *B01L 3/00* (2006.01)
  *B01L 9/00* (2006.01)
  *G01N 21/03* (2006.01)

(56) References Cited

U.S. PATENT DOCUMENTS

| | | |
|---|---|---|
| 7,268,552 B1 | 9/2007 | Gerald, II et al. |
| 2003/0106382 A1 | 6/2003 | Shukla et al. |
| 2004/0091401 A1* | 5/2004 | Golabek et al. ............... 422/102 |
| 2010/0184056 A1* | 7/2010 | Weinberger et al. .............. 435/6 |
| 2012/0094373 A1* | 4/2012 | Su et al. ..................... 435/304.1 |
| 2013/0071917 A1* | 3/2013 | Su et al. ..................... 435/304.1 |

OTHER PUBLICATIONS

Communication pursuant to Article 94(3) EPC for European Patent Application No. 11 182 639.2-1356, dated Nov. 4, 2015, 3 pages.

* cited by examiner

DEVICE FOR DETECTING PROPERTIES OF CHEMICAL AND/OR BIOLOGICAL FLUIDS

CROSS-REFERENCE TO RELATED APPLICATION

The present application claims the priority of European patent application Ser. No. 11 18 2639.2, filed Sep. 23, 2011, the content of which is hereby incorporated by reference in its entirety.

The present invention relates to a device for investigating, measuring and/or detecting properties of chemical and/or biological fluids. In particular, the present invention relates to a device for performing these procedures and a system comprising a holder for holding at least one of said devices.

BACKGROUND OF THE INVENTION

For the analysis of liquids, in particular in bio-analytics, it is necessary to pick up defined small volume of liquids in a container, to transport the liquid and to analyze the liquid. For this process of manipulation, transportation and analysis of liquids in the container conventional methods only use mechanical forces and pressure differences. These conventional forces bare the risk to damage the liquid containing structure, for example mechanical and pressure forces can break glass capillaries. This may cause problems as biological liquids may be hazardous, expensive and/or laborious to obtain. Breaking the liquid container may therefore result in additional work, costs and risks for the user.

Furthermore, the conventional ways to hold samples in place mainly comprise mechanical means. In addition to the aforementioned problems, further problems arise of the samples and/or the samples not being in a precisely defined position when measurement is performed. This may result in inaccurate measurements. This is particularly problematic when the measurement comprises optical investigation of the sample. Due to this, time consuming and costly re-measurement may be required. Also devices using mechanical means to manipulate samples have to fit exactly to the geometry of the sample container. Thus for every different sample container geometry a different mechanical adapter is needed, restricting the economic use to a very limited range of sample container geometries and sizes.

It is an object of the present invention to overcome or ameliorate these obstacles. In particular, it is an object to provide a device which allows for easy to use measurement of chemical and/or biological fluids. It is a farther object to provide a device which allows for these fluids to be conveniently and precisely positioned in a holder to perform optical measurements of said fluids.

The objects of the invention are accomplished by the independent claims. Further preferred embodiments are defined by the dependent claims.

SUMMARY OF THE INVENTION

The present invention relates to a device for detecting properties of chemical and/or biological fluids. The device comprises a tubular structure with a cavity and/or a bore for accommodating the fluid. The device further comprises a magnetizable and/or magnetic material, wherein the tubular structure comprises at least one segment that is transparent to light, preferably with a wavelength in a range of about 200 nm to 2000 nm. A magnetizable and/or magnetic material is any material which is susceptible to manipulation with a magnetic force. Fluids refer to both gases and liquids. The fluids preferably comprise chemical and/or biological liquids and more preferably chemical and/or biological samples in solution. More preferably, the liquid samples comprise a solvent, which may be most preferably an organic solvent or water. In other words, the chemical and/or biological samples in solution may comprise an aqueous solution, an organic solution, a biological liquid like whole blood, blood serum, blood plasma, lysate and the like. In still other words, it may be the liquid itself which is to be investigated or it may be a solution containing samples, molecules and/or particles which are to be investigated.

The device in accordance with this invention can have different states, that means the tubular structure, can be empty, it can be partially and/or completely filled with said fluid. Preferably, the tubular structure is a capillary and is preferably made of glass and/or one or more polymers.

It is further preferred that said tubular structure comprises the magnetizable and/or magnetic material.

It is preferred that at least one segment (portion) of the tubular structure is transparent to light of wavelength of 200 nm to 900 nm, preferably 250 mn to 900 nm, preferably 275 nm to 850 nm. More preferably, but not restricted to, said at least one segment is transparent to light of one or more of the following wavelength regimes: 940 nm to 1040 nm (preferably 980 nm +/−10 nm), 1150 nm to 1210 nm, 1380 nm to 1600 nm (preferably 1450 nm +/−10 nm and/or 1480 nm +/−10 nm and/or 1550 nm +/−10 nm), 1900 nm to 2000 nm (preferably 1930 nm +/−10 nm). It will be understood by the person skilled in the art that the transparent segment(s) may also refer to the whole tubular structure. In other words, the whole tubular structure may be transparent.

The transparency of the segment may allow for fluorescence/phosphorescence and/or absorption measurements and/or optical investigation/measurement and/or manipulation of the solution/liquid and/or gas (fluid) inside the cavity of tubular structure. The transparency may further allow for fluorescence measurement. In a preferred embodiment, it may also allow for optical laser heating (preferably infrared (IR)) of the fluids inside the tubular structure, preferably for heating of water and/or organic solvents.

The magnetizable and/or magnetic material may be provided on the inner wall of the tubular structure, on the outer wall of the tubular structure, within a wall of the tubular structure and/or at an end or both ends of the tubular structure.

The magnetizable and/or magnetic material may be paramagnetic, ferromagnetic or diamagnetic.

According to one embodiment of the invention, the inventive device comprises a magnetic material/material which is susceptible to manipulation/interaction/handling with a magnetic force. Thus the device can be manipulated with a magnetic force/field. This manipulation can be, but is not limited to, to pick up the device using a magnetic force, to hold the device using a magnetic force, to move the device using a magnetic force, to rotate the device using a magnetic force, to position the device using a magnetic force, to align the device using a magnetic force, to fixate the device using a magnetic force, to remove the device using a magnetic force and/or to release the device using a magnetic force and/or combinations of the previous. Said device allows for the magnetic manipulation, transportation and analysis of said fluids. As no or only small mechanical forces and pressures are applied, a damage of the liquid containing tubular structure can be prevented, thus allowing for the use of very small, thin, fragile and flexible structures and materials. By this, the tubular structure can be very small, allowing very small amounts of fluids, preferably liquids to be investigated. Furthermore, the device can be manipulated (e.g. orientated, fixed) without the need of touching it. By using magnetic forces, the devices can be hold in any desired position. In a preferred embodiment the magnetizable and/or magnetic material is at least one of the group consisting of a, preferably metallic, clip, a, preferably metallic, plug/stopper to partially or entirely seal the tubular structure, a, preferably, magnetic paint, a composite material and a compound material. More preferably, the compound/composite material comprises a polymer material, most preferably polypropylene, Acrylonitrile butadiene styrene (ABS), Polycarbonates (PC), Polyamides (PA), Polybutylene terephthalate (PBT), Polyethylene terephthalate (PET), Polyphenylene oxide (PPO), Polysulphone (PSU), Polyetherketone (PEK), Polyetheretherketone (PEEK), Polyimides Polyphenylene sulfide (PPS), Polyoxymethylene plastic (POM), Polylactide (PLA), polyvinyl alcohol plastic (PVA).

Composite materials, often shortened to composites or called composition materials, are typically engineered or naturally occurring materials made from two or more constituent materials with significantly different physical or chemical properties which remain separate and distinct or substantially separate and substantially distinct at the macroscopic and/or microscopic scale within the finished structure. The terms compound material and composite materials are interchangeably used in the present application, i.e., all embodiments which refer to a compound materials may be replaced with embodiments which correspondingly refer to composite materials and vice versa.

Furthermore, the term compound material is not limited to composite materials with separate and distinct material regions at the macroscopic and/or microscopic scale within the finished structure. The person skilled in the art will understand that the term compound material relates to composite materials with separate and distinct regions at the macroscopic and/or microscopic scale within the finished structure or without separate and distinct regions at the macroscopic and/or microscopic scale within the finished structure. In other words, compound materials may be defined as materials which combine two or more sub-materials.

The magnetic material may be a paint, a coating, a lacquer, a clip, a compound and/or composite material (for example a material which combines two or more sub materials), a label/tag/adhesive label, a plasticise/modeling material, a plug, a wax, a belt/bend/cord, a metallic clip and/or also combinations of these. The magnetic material may also be a doping, addition, alloy and/or an intermixture to the tubular structure. Preferably, the magnetic material comprises a magnetic paint. The magnetic material may be applied at a certain segment of the device. The segment may span full 360 degrees (preferably of the circumference) of the tubular structure or only a part thereof (10 degrees to 270 degrees). The magnetic material can also be transparent. It is preferred that the compound material (in other words, the composite material) has a multifunctionality which is most preferably also determined by its composition. It may have a certain shape to position and/or manipulate the device mechanically. The shape of the compound material may be conus-shaped, cylindrically shaped, hexagonal shaped, U-shaped, V-shaped and the like. It may also promise threads and/or boles. The compound material may also be provided as a belt/bend/cord containing one, two, a plurality of capillaries/tubular structures. The compound material may also have a certain color, to color-code different embodiments of the devices. The compound material also may have a "magnetic barcode", that is sectors/segments with different magnetization which may code for different embodiments of devices and may be read out by a reader.

The magnetic material may have electrical properties like an insulator, a semi-conductor or a conductor.

Compound material may be composed of different materials of different particle size I grain size and/or grain shape/particle shape. Preferably the compound material may also is have a thermal conductivity, preferably in the range of 0.004 W/(m K) to 2000 W/(m K), more preferably in the range of 0.1 W/(m K) to 410 W/(m K), most preferably in the range of 0.2 W/(m K) to 200 W/(m K). The compound/material may have an average wall thickness of 0.001 mm to 3 mm, preferably of 0.01 mm to 2 mm, more preferably of 0.1 mm to 1 mm.

In a preferred embodiment, the compound material provides an optical, electrical and/or magnetic. characteristic.

The tubular structure of the device according to the present invention may have a length of 1 mm to 100 mm, preferably of 20 mm to 100 mm, more preferably of 20 mm to 70 mm.

The segment of the tubular structure comprising the magnetic material may have the same length as the tubular structure or a shorter length or a longer length. Preferably the segment comprising the magnetic material has a length of 0.1 mm to 100 mm, more preferably of 1 mm to 30 mm.

The tubular structure of the device according to the present invention may have a cross-section or outer diameter of 0.01 mm to 5 mm, preferably of 0.1 mm to 2 mm, more preferably of 0.1 mm to 1 mm. The shape of the cross section of the tubular structure may be circular, oval, triangular, quadratic, rectangular, hexagonal and/or combinations of these. It may also be basically round/circular with one or more flattened sides. This may be advantageous, as the tubular structures cannot roll when having at least one flattened side. Preferably, the outer diameter or cross sectional shape of the tubular structure is constant over the entire length of the tubular structure. According to other preferred embodiments, however, it may be preferred that the outer diameter decreases at least at one end portion of the tubular structure. Such tubular structures with a tapered outer diameter may be advantageous for vertical placement in a corresponding holder.

The tubular structure of the device according to the present invention may have a wall thickness of 0.001 mm to 2 mm, preferably of 0.01 mm to 1 mm and more preferably of 0.01 mm to 0.49 mm. Preferably, the wall thickness of the tubular structure is constant over the entire length of the tubular structure. According to other preferred embodiments, however, it may be preferred that the wall thickness decreases at least at one end portion of the tubular structure and/or in the center of the tabular structure.

The inner diameter of the tubular structure is preferably in the range from 0.02 mm to 4.99 mm. Preferably, the inner diameter of the tubular structure is constant over the whole length of the tubular structure. According to other preferred embodiments, however, it may be preferred that the inner diameter decreases at least at one end portion of the tubular structure.

According to a further embodiment of the present invention the inner walls of the tubular structure can also be modified chemically and/or physically and/or structurally. The modification of the inner walls of the device may be used to control the hydrophobicity, hydrophilicity, capillary forces/capillary action and/or the surface tension and/or the sticking of biomolecules and/or solution. According to the present invention the inner walls of the tubular structure can also be modified covalently and/or non covalently and/or by adsorption., with polymers, biomolecules, aminoacids, antibodies, proteins, nucleodites, oligonucleotides, DNA, RNA, PNA, LNA, peptides, antigens,L-lysin, poly-L-lysin, aptamers, cells, lipids and the like. The person skilled in the art understands that the term modification includes the process of immobilization. The modification can also be spacely different, for example modification patterns and/or modification gradients can be used.

The person skilled in the art understands that the term "magnetic forces" comprises attractive and repelling forces and different combinations/superposition of different and/or similar attractive and/or repelling forces. The person skilled in the art also understands that magnetic forces are generated by magnetic fields.

It is preferred that the tubular structure is a capillary. It is further preferred that the tubular structure comprises glass and/or a polymer and/or at least one of borosilicate, borosilicate 3.3 (for example DURAN-glass), quartz glass like suprasil, infrasil, synthetic fused silica, soda-lime glass, Bk-7, ASTM Type 1 Class A glass, ASTM Type 1 Class B glass. The polymer may comprise PTFE, PMMA, Zeonor™, Zeonex™, Teflon AF, PC, PE, PET, PPS, PVDF, PFA, FEP, and/or acrylic glass. As very small and thin structures can be used, it is possible to transport and manipulate very small volumina, which is advantageous especially in bio-analytics and diagnostics. As the walls of the tubular structure can be very thin, they often comprise a high transparency for light of wavelength 200 nm to 2000 nm and thus thin walls are advantageous for the optical analysis (fluorescence, absorbance) of molecules in the liquids.

Additionally the magnetic material of the device can comprise information which is stored and/or coded magnetically, for example magnetic sectors with alternating magnetization/magnetic resistance. Thus the device according to the present invention can not only be used for manipulation and analysis of liquids and/or solutions but can also be used to store information for example about its parameter like inner diameter of the tubular structure or store individual information of the sample, e.g., as an individual tag.

The magnetic properties of the device according to the present invention can also be used to detect the device, for example by a "magnetic feedback", preferably by induction when the device is placed to a holder containing a coil/inductor.

The optical, electrical and/or magnetic characteristic may comprise a code and/or identifier, allowing for an identification, discrimination, coding and/or detection of the device and/or different embodiments of the device. For example, but not limiting to, the code can be a magnetic code and/or color code and/or electrical code. Preferably the magnetic material comprises the code. For example, the magnetic code can be a sequence of equally and/or differently directionally magnetized sectors of a magnetic material, for example the sequential changes in the direction of magnetization can represent patterns of binary data bits which can be read out by a reader.

In a preferred embodiment, the optical characteristic is provided by specific colors or pattern like 1D or 2D barcodes; the electrical characteristic is provided by conductivity, conductivity pattern; and/or the magnetic characteristic is provided by a magnetic pattern with at least two sectors of different magnetic properties like different magnitude of the magnetic force and/or different polarity of the magnetic field.

It is also preferred that at least one end portion of the tubular structure and/or the magnetizable and/or magnetic material comprises a form, preferably a tapered form, which matches a form on a corresponding holder to provide a positive fit/form closure. This may allow the device to be easily positioned in the correct position, e.g., in a vertical position.

It may also be preferred to provide a bunch/bundle comprising a plurality of device according to any of the preceding claims, wherein the devices are connected/bundled by means of a belt/strap and/or bundled in a drum. By doing this, one may conveniently test a multitude of different devices.

In addition to the device aforementioned, the present invention also relates to a system for manipulation of at least one of the devices, comprising one or a plurality of elements allowing for an interaction and manipulation of one or a plurality of the devices via magnetic forces/fields. The system may also be used to detect the device via magnetic interaction and/or to read out magnetic codes.

The system may comprise a holder with one or a plurality of holding elements to hold the device at a predetermined position with a predetermined magnetic force. The elements may be magnets, for example permanent and/or non permanent magnets.

The system may also comprise a manipulator, with one or a plurality of manipulation elements to manipulate the device(s). Preferably, the manipulator is adapted to pick up and/or to move and/or to rotate and/or to hold and/or to orient and/or to release The device(s). Again, the manipulation elements may be magnets, for example permanent and/or non permanent magnets, preferably electromagnets.

In a preferred embodiment, the invention relates to a holder for holding a device with aforementioned properties, wherein the holder comprises a single or a plurality of permanent and/or electro magnet(s) for magnetically interacting with the magnetizable and/or magnetic material of the tubular structure.

According to the present invention, permanent and/or electro magnets may be used for magnetically engaging or interacting with the magnetizable and/or magnetic material. The magnetic interaction between the holder and the magnetizable and/or magnetic material on the tubular structure provides several advantages. For instance, by means of the magnetic interaction the tubular structures can be positioned, preferably very exactly at a desired location on the holder. The magnetic interaction preferably holds or fixes the tubular structure with a force sufficient to avoid accidental release of the tubular structure.

In other words, the magnets) is/are adapted to interact with magnetic/magnetizable material of the device to secure/hold/position the device at a predetermined position.

The magnetic force acting on the magnetic material may be generated by a magnet. The magnet may be a permanent magnet and/or a non-permanent magnet and/or a combination of them and/or pluralities of them. Preferably the magnet is an electromagnet. In a preferred embodiment, the magnet comprises a coil. In such a coil, the magnetic force may be controlled by the current flow through the coil. This may allow for conveniently manipulating the force acting on the magnetic material. By switching the current on and off, one may switch the force between the coil and the magnetic material on and off. Furthermore, one may also use such a coil to detect the presence of the magnetic material inductively. In a preferred embodiment this may be used to detect the presence of the device according to the present invention. The person skilled in the art also understands that the term "magnet" comprises dipole magnets, quadruple magnets and the like. Preferably the magnetic force acting on the device/capillary is controllable, for example the magnetic force is generated with an electromagnet, for example a coil/inductor, and the magnetic force may be changed by changing the electric current through the coil. The magnetic force may be used to manipulate the device/capillary/tubular structure, for example to hold and/or to fix and/or to move, and/or to rotate and/or to orient the device to and/or at a defined position.

As magnetic forces, in particular magnetic forces generated by an electromagnet, can be easily controlled by electric current, the magnetic forces can be well adapted to the tubular structure to be transported. The magnetic forces can be switched on by applying an electrical current, switched off by switching off the electrical current and also continuously varied by varying the electrical current By switching the magnetic force on and off, it is preferably possible to perform one or more of the following with the devices: pick up the device, move the device, position the device, align the device, fixate the device, remove the device and release the device. It will be clear to those skilled in the art that it may also be preferred to perform these actions with different devices simultaneously. That is, switching the magnet(s) on and off may preferably result in one or more of the devices being picked up etc. The magnetic forces acting on a capillary, for example for the fixation of the capillaries to the holder, are preferably in the range of 0.00001 N (Newton) to 100 N, more preferably in the range of 0.0001 N to 10 N, more preferably in the range of 0.001 N to 1 N.

Furthermore, the holder or the measuring device may be provided with a detector for detecting the magnetize/magnetizable material. The detector may simply detect the presents or absence of a tubular structure at a predetermined position. The detector may, however, also detect a predetermined (preferably individual) characteristic of the tubular structure.

The detection of the individual characteristic may be based on magnetic properties, on the detection of individual magnetic pattern, optical pattern and the like.

Without restricting it to this usage, the device in accordance with this invention may be used the following ways:
1. General Example of Usage An empty device or a plurality of devices is provided in a tray or at a belt. The empty device is picked up magnetically using a magnetic force, for example by switching on the current through a coil. The device is magnetically clamped by the magnetic force and is transported to a reaction tube or multiwell plate containing the solution. The device is partially moved into the solution. The solution is sucked into the cavity of the device by capillary forces/capillary action or actively with a pump. The filled device is moved out of the solution. The filled device is transported to a device holder which is used to place the device to investigate the solution inside the device. The device is placed at the holder. At the holder the device is released by switching off the magnetic force. At the holder, which comprises magnets, the device is positioned and fixed again magnetically by a defined magnetic force. The device is moved by the holder to a detector by which the solution inside the device is investigated optically through a transparent segment of the device. This investigation may be repeated for several times. After the investigation the device is moved out of the place of investigation and the magnetic force, holding the device magnetically, is switched off to release the device, for example to dispose the device, though it may also possible to reuse the device.

2. Detailed Example of Usage: Microscale Thermophoresis (MST)/Therma-Optical Measurement With Device A serial dilution of a not labeled molecule is prepared, spanning a concentration range from about 20× the expected KD, down to substoichiometric concentrations with respect to the concentration of the labeled molecule. Following this, an equal volume of fluorescently labeled molecule with a concentration in the range of 1-100 nM is added and care is taken to that the liquids are mixed well. The samples are incubated for a time sufficient to reach the equilibrium of the binding reaction.

The box with capillaries is openend an capillaries are carefully taken out of the box. Care is taken that the glass of the capillaries is not touched, and instead the capillaries are moved by using the magnetic part as a handle.

The capillaries are either placed directly in the micro reaction cup with the glass end of the capillary first (i.e. not the end carrying the magnetic modification).

Alternatively, when the sample is applied in a multiwell-plate, the capillaries are first placed on a magnetic multi capillary holder system. It positions the capillaries in distances, suited for a 96, 384 or 1536 well plate. A variable number of capillaries (up to 8, 16, 24, 32, 48, 64, 96, 128) is placed on the holder and the capillaries are placed simultaneously in the well plate The capillaries are filled by capillary forces. If they are not filled properly, e.g. half of the length, the capillary is slightly moved within the micro reaction tube/multi well plate or capillaries and sample are positioned horizontally to ease filling of the capillary.

Depending on whether the capillary holder is used or not, the capillaries are either placed manually on the tray, or all capillaries are placed altogether on the tray by using the magnetic capillary holder.

Care is taken that the part of the capillary that is in the center position of the tray, contains liquid and no airbubble. Therefore the capillaries can also be moved laterally on the tray.

The sample tray is inserted in the instrument.

The capillary scan is started and the concentration in each capillary is denoted in the control software. By detecting the magnetic force, the instrument automatically senses the number of capillaries on the tray and adjusts the scan width accordingly.

One or more measurements are performed per capillary.

After the measurement, the tray is removed from the instrument and capillaries are removed with or without using the magnetic capillary holder device in a container for glass waste and sharps.

Still further objects, features and advantages of the present invention will become evident to those skilled in the art with the following drawings, which serve the sole purpose to illustrate preferred embodiments of the invention and do not by any means limit the scope of the invention.

DETAILED DESCRIPTION OF THE DRAWINGS

Figure 1:
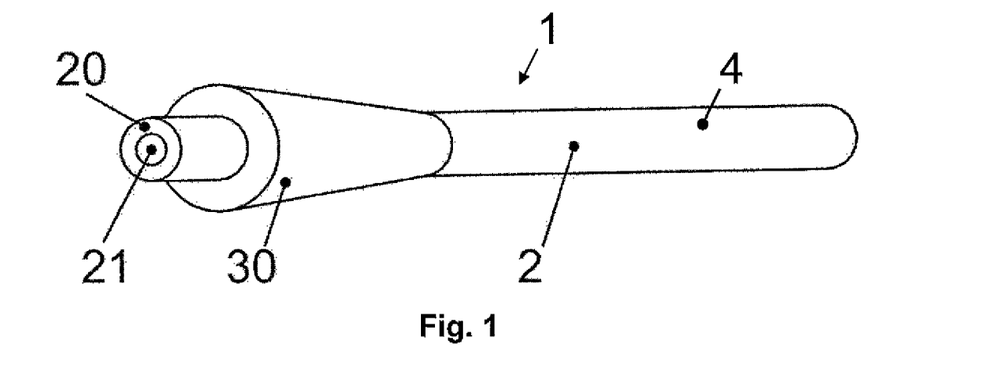
FIG. 1 shows a perspective view of an embodiment of a device according to the present invention.

FIG. 1 shows a perspective view of a device 1 according to the present invention where the tubular structure 2 is a transparent capillary and the magnetic material 30 is a tapered magnetic and/or magnetizable material at the outer wall 20 of the tubular structure. The device 1 further comprises a cavity 21 for accommodation of a chemical and/or biological fluid. Preferably, the fluid is a liquid. Examples for this liquid include, but are not limited to, aqueous solutions, organic solutions, blood, blood serum, blood plasma, lysate and the like. The tapered magnetic material and/or magnetizable material 30 is formed in this shape to allow for simple and easy to use handling and orientation of said device.

The magnetic material, preferably the magnetic compound material at the outer wall of the capillaries may also be advantageous for the manual handling of the device. As the magnetic material can be touched with the fingers, the magnetic material may protect the thin and transparent tubular structured from autofluorescent fingerprints and mechanical pressure. The magnetic material may also be shaped in such a way that it can be well handled.

Figure 2:
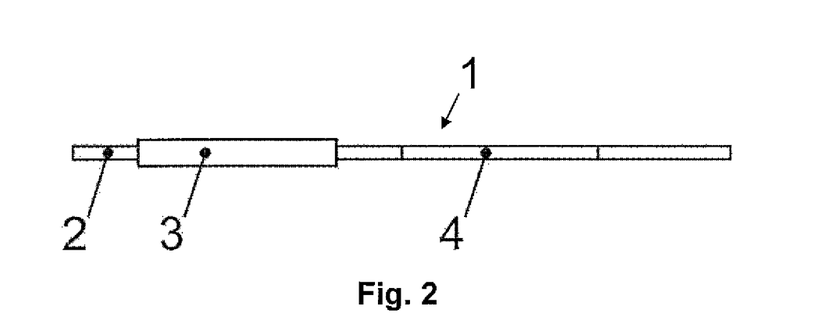
FIG. 2 shows an elevational view of another embodiment of a device according to the present invention.
Figure 3:
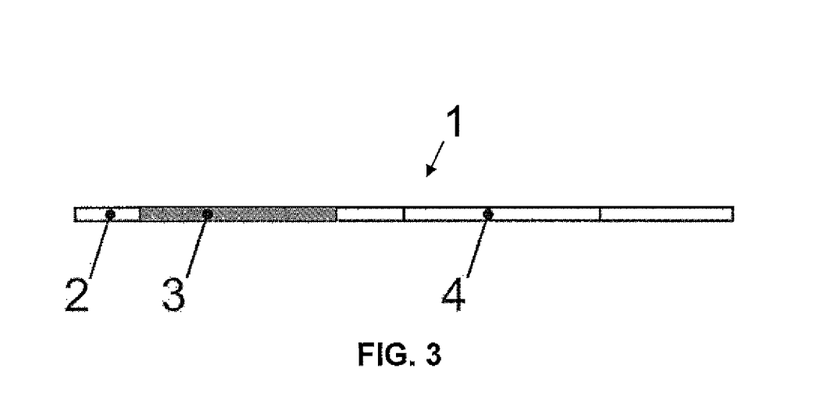
FIG. 3 is an elevation view of yet another embodiment of the device of the present invention.
Figure 4:
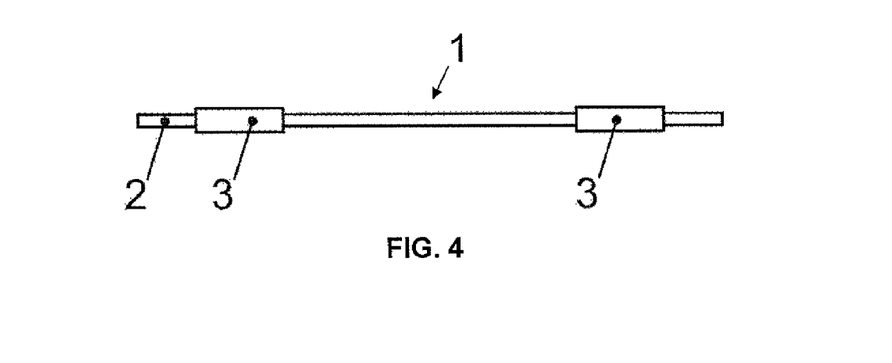
FIG. 4 is an elevational view of yet another embodiment of the device of the present invention.
Figure 8:
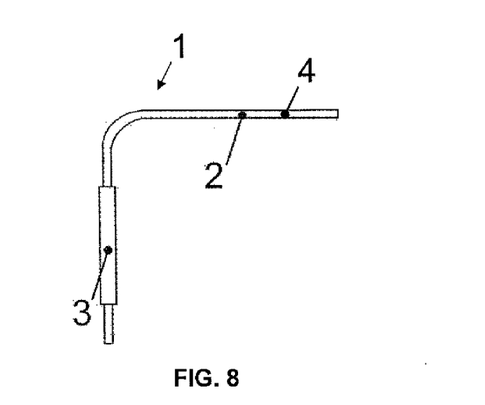
FIG. 8 shows an elevational view of yet another embodiment of a tubular structure with a curvature according to the present invention.

FIG. 2 shows an elevational view of another embodiment of a device 1 according to the present invention. In this embodiment, the device 1 comprises a tubular structure 2, a magnetic material 3 at the outer wall of the tubular structure and a transparent segment 4 of the tubular structure, wherein the magnetic material 3 has basically the same shape as the tubular structure, that is here cylindrical. The magnetic material 3 may be used to hold the tubular structure in a certain position when fluids, preferably liquids in the tubular structure are investigated. For investigation, light is shined onto the fluids in said tubular structure through the transparent segment 4. However, the magnetic material does not need to be at the outer wall of the tubular structure. In another embodiment and as depicted in FIG. 3, it may also be preferred that the magnetic material 3 is at the inner all and/or within the wall of tubular structure 2. Again, the tubular structure 2 in FIG. 3 comprises a transparent segment which preferably allows to shine in light and/or to investigate the fluid in said tubular structure. This may have the advantage that it might be easier to manufacture such a device with a constant cross sectional diameter if desired. Referring now to FIG. 4, it becomes apparent to those skilled in the art that the magnetic material may also be at two (or more) different positions of the tubular structure. The embodiments of the tubular sections depicted in FIGS. 1-4 are of generally straight or linear shape. Furthermore, it may also be-preferred to provide the tubular structures in a curved shape. Referring to. FIG. 8, there is another embodiment of the device 1 of the present invention comprising a tubular structure 2 with a curvature, a transparent section 4 and a magnetic material 3. Preferably, the tubular structure 2 is a capillary.

Figure 5:
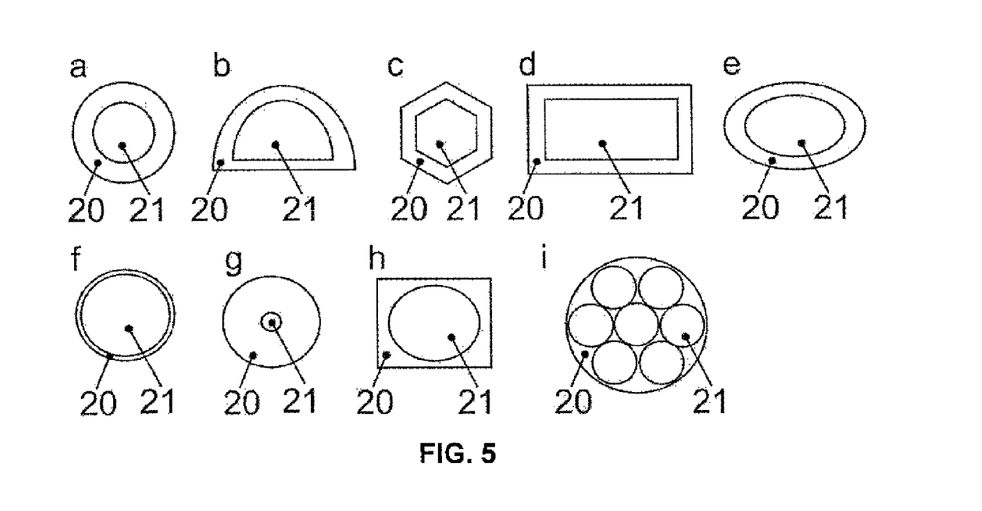
FIGS. 5a-i show cross sectional views of different embodiments of the device of the present invention.

Referring now to the cross section of said tubular structures and also referring to FIG. 5, it becomes apparent that there is a multitude of different cross sections which may be used in the context of this invention. As depicted in FIGS. 5*a* through 5*i*, the tubular structures comprise a wall 20 (which is preferably made of glass or polymer material) and a cavity 21. For different applications and samples, different cross sections may be preferred. The cross sections may be round (FIG. 5*a*), round with one flat side (FIG. 5*b*), hexagonal (FIG. 5*c*), rectangular (FIG. 5*d*) and/or elliptical (FIG. 5*e*). Furthermore, the wall thickness may be chosen according to the application to be thinner (FIG. 5*f*) or thicker (FIG. 5*g*). It may also be preferred that the cross sectional shapes of the cavity 21 and the wall 20 are of different shapes, e.g. a elliptical cross section of cavity 21 and a rectangular cross section of wall 21 as depicted in FIG. 5*h*. In yet another embodiment of the present invention, the tubular structure may also comprise a plurality of cavities 21 (FIG. 5*i*). The round cross section as in FIG. 5*a* might be preferred as it might be easier (and therefore cheaper) to manufacture and produce such a device. The devices comprise at least one flattened side when viewed in cross section (that is the embodiments depicted in FIGS. 5*b* through 5*d* and FIG. 5*h*) may be preferred as a flattened side prevents the device from rolling. That is, these devices are more easily immobilized than devices having a generally elliptic or circular cross section. The difference in wall thickness (see FIGS. 5*a*, 5*f*, 5*g*) may have certain, advantages and disadvantages with respect to manufacture, measuring and handling. The thicker the wall thickness, the more material is needed to manufacture said device. Generally, the thinner the walls, the more fragile the devices are. That is, the thinner the walls, the more care must be taken when handling said device.

Thin walls can be preferable in terms of the higher optical transmission, as optical absorption follows the law of Beer-Lambert with $I/I0=\exp(-d/\text{sigma})$ where $I0$ is the optical intensity before the electromagnetic radiation enters the wall, I is the intensity after the electromagnetic radiation passed the wall, d is the wall thickness and sigma is the absorption coefficient of the wall material.

The wall thickness also determines the heat capacity of the tubular structure, the heat conductivity and the heat diffusion relaxation time. Thinner wall may have a faster heat diffusion relaxation time, that means the heat transport to the fluid inside the tubular structure is faster. This may be advantageous for example if the device is used for a polymerase chain reaction (PCR) where fast heating and cooling of a fluid is preferable.

The wall thicknesses determines the magnitude of the autofluorescence signal for autofluorescent wall material. Thinner walls may be preferable to reduce the auto-fluorescence signal/background for fluorescence measurements. For example it is preferable for auto-fluorescence reduction to use thin walls below 0.1 mm thickness for fluorescence measurements with short wavelength of electromagnetic radiation, for example with excitation below 350 nm (for example ultraviolet excitation).

Figure 6:
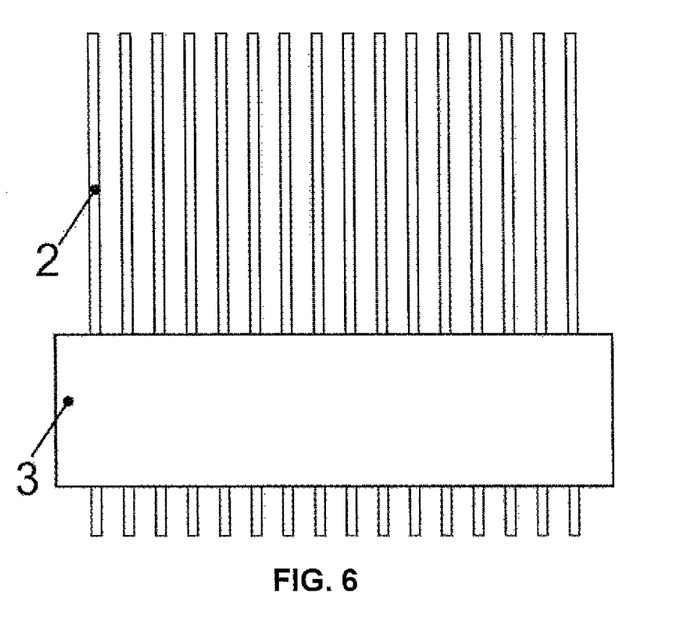
FIG. 6 is an elevational view of an embodiment of a holder containing a plurality of tubular structures according to the present invention.

Referring now to FIG. 6, it may also be preferred to provide a plurality of tubular structures 2 which are embedded in a magnetic material 3. Preferably, these tubular structures are equally spaced from each other. Preferably 8, 12, 16, 24, 32 or 48 capillaries are embedded equally spaced in a magnetic material, preferably with a mid-to-mid distance of 2.25 mm, 4.5 mm or 9 mm.

Figure 7:
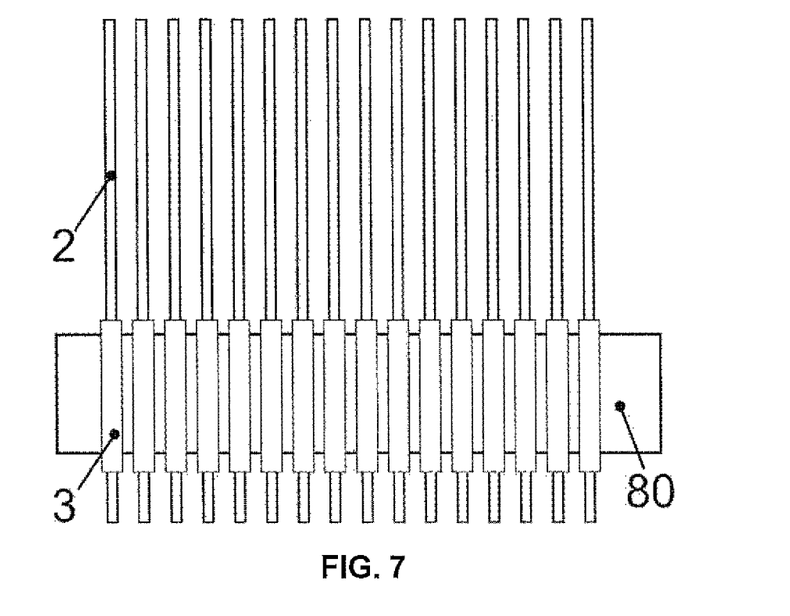
FIG. 7 is an elevational view of yet another embodiment of a holder containing a plurality of tubular structures according to the present invention.

Reference is now made to FIG. 7. Instead of embedding the tubular structures in one piece of magnetic material, it may also be preferred to fix tubular structures generally similar to those in FIG. 2 to a supporting element 80. It is preferred that supporting element 80 is a flexible belt and/or a rigid material. Instead of fixing the tubular structures onto a generally 2-dimensional supporting element, it may also be preferred to fix the tubular structures onto a cylinder and/or a drum (not shown).

Figure 9:
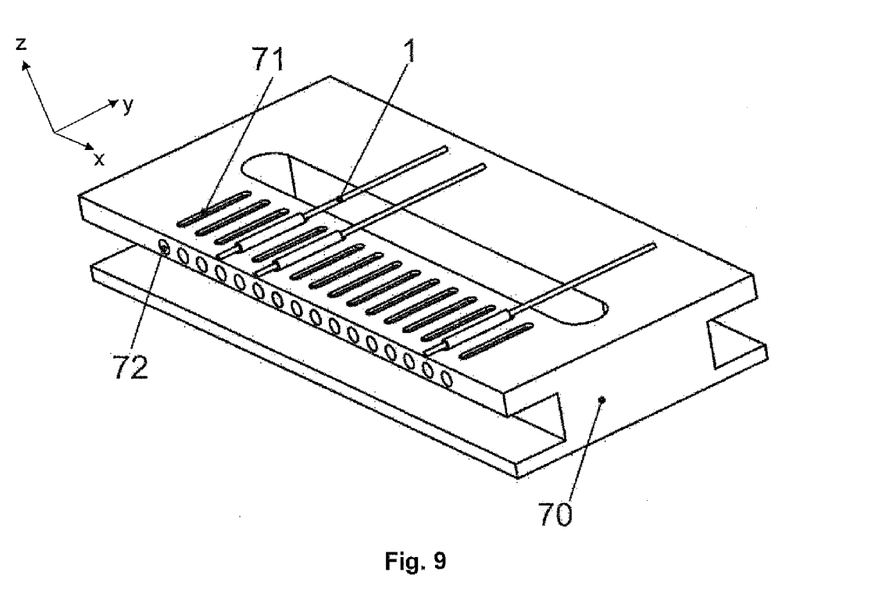
FIG. 9 shows a perspective view of a holder for a plurality of devices according to the present invention.

As described in greater detail in the aforementioned examples, said tubular structure may be placed on a holder, preferably by a magnetic force. Reference is now made to FIG. 9, which shows an embodiment of such a holder 70 which is adapted to hold a plurality of the devices 1 according to the present invention. The holder may comprise slots 71 for positioning the devices 1 and magnets 72 for fixation of the devices 1. The slots, however, maybe omitted depending on the magnetic forces for the fixation of the devices at the top surface of the holder. These magnets preferably comprise permanent magnets and/or electromagnets 72. Preferably the electromagnets are coils which can be switched on and off by the current flow through the coils. The plurality of coils may be controlled and energized commonly all together. According to another preferred embodiment it may be preferred to control some or all coils individually such that an individual fixation or release of the devices is possible. This may allow for simple and convenient fixation and release of said devices. Though the devices 1 are shown to be positioned in a generally two dimensionally manner on holder 70, the invention is by no means limited to this configuration. For instance, FIG. 9 shows the devices 1 placed in the horizontal x-y plane, wherein the z-axis is parallel to the axis of the gravitational force. Other preferred embodiments of the holder include cylindrical and/or drum-shaped holders (not shown). For example, holders with horizontally places devices or vertically (along the z-axis) placed devices 1 may be used for measurements.

Figure 10:
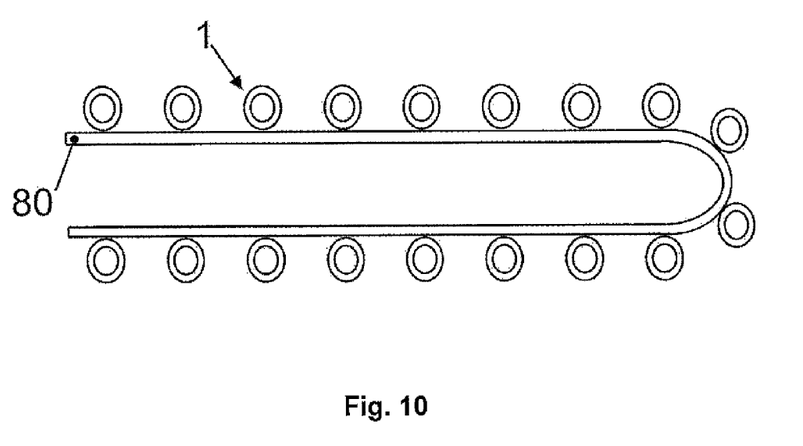
FIG. 10 shows a perspective view of a belt/cord for a plurality of devices according to the present invention.

FIG. 10 shows a perspective view of a belt/cord 80 for a plurality of devices 1 according to the present invention. The belt can be an "endless" belt. According to other preferred embodiments, the belt can also be provided in a magazine and/or may have holes within the belt for picking and moving it, e.g., the belt may work like a conveyor. Benefits of such belts may be less required amount of space for storing and/or transporting a plurality of devices compared to a rigid support. The belt design may be further advantageous for high throughput where hundreds or thousands of capillaries are needed.

While the invention has been described with reference to the exemplary embodiments thereof, those skilled in the art will be able to make various modifications to the embodiments without departing form the true scope of the invention. The terms and descriptions used herein are set forth by way of illustration only and are not meant as limitations. Those skilled in the art will recognize that variations are possible within the scope as defined in the claims and their equivalents.

The invention claimed is:

1. A capillary for detecting properties of chemical and/or biological fluids, said capillary comprising:
   a cavity for accommodating the fluid;
   a magnetizable and/or magnetic material fixed connected to the capillary; and
   a segment that is transparent to light of wavelength 200 nm to 2000 nm.

2. The capillary of claim 1, wherein the capillary is a tubular structure.

3. The capillary of claim 1, wherein the magnetizable and/or magnetic material is provided
   a) on the inner wall of the capillary,
   b) on the outer wall of the capillary,
   c) within a wall of the capillary, and/or
   d) at an end of the capillary.

4. The capillary according to claim 1, wherein the capillary is 1 to 100mm in length, 0.01 to 5 mm in cross section and 0.001 to 2 mm in wall thickness.

5. The capillary according to claim 1, wherein the magnetizable and/or magnetic material is at least one of the group consisting of a ring, a clip, a plug/stopper configured to partially or entirely seal the tubular structure, a paint and a compound material.

6. The capillary according to claim 5, wherein the compound material comprises a polymer material and/or a metallic material, and/or wherein the compound material comprises at least one of the group consisting of polypropylene, Acrylonitrile butadiene styrene (ABS), Polycarbonates (PC), Polyamides (PA), Polybutylene terephthalate (PBT), Polyethylene terephthalate (PET), Polyphenylene oxide (PPO), Polysulphone (PSU), Polyetherketone (PEK), Polyetheretherketone (PEEK), Polyimides Polyphenylene sulfide (PPS), Polyoxymethylene plastic (POM), Polylactide (PLA), and polyvinyl alcohol plastic (PVA).

7. The capillary according to claim 5, wherein the compound material provides an optical, electrical and/or magnetic characteristic.

8. The capillary according to claim 7, wherein:
   a) the optical characteristic is provided by specific colors, a pattern, a 1D barcode, or a 2D barcode;
   b) the electrical characteristic is provided by conductivity, or conductivity pattern; and/or
   c) the magnetic characteristic is provided by a magnetic pattern with at least two sectors of different magnetic properties.

9. The capillary according to claim 1, wherein at least one end portion of the tubular structure and/or the magnetizable and/or magnetic material comprises a form, which matches a form on a corresponding holder to provide a positive fit/form closure.

10. The capillary according to claim 1, wherein the cavity is a tubular cavity comprising at least partly a circular, polygonal, oval cross section and/or a cross section with at least one flat side.

11. A bunch comprising a plurality of capillaries according to claim 1, wherein the capillaries are
   a) bundled by means of a belt or strap; and/or
   b) bundled in an envelope.

12. A holder holding a capillary according to claim 1, wherein the holder comprises a single or a plurality of permanent or electro magnet(s) for magnetically interacting with the magnetizable and/or magnetic material of the capillary.

13. The holder according to claim 12, wherein electro magnets are individually and/or commonly controllable.

14. The holder according to claim 12, wherein the magnetic force acting on the capillary is in a range selected from the group consisting of 0.00001 N to 100 N, 0.0001 N to 10 N, and 0.001 N to 1 N.

15. The device according to claim 2, wherein the capillary comprises at least one of borosilicate, borosilicate 3.3, quartz glass, suprasil, and infrasil.

16. The device according to claim 2, wherein the capillary comprises a polymer.

17. The capillary according to claim 1, wherein the capillary has a constant inner diameter along the whole length of the capillary.

18. The capillary according to claim 17, wherein the outer diameter or cross sectional shape of the capillary is constant over the entire length of the capillary.

19. The bunch according to claim 11, wherein the capillaries are bundled in a drum.

* * * * *